United States Patent [19]

Sehgal et al.

[11] 4,230,692

[45] Oct. 28, 1980

[54] RAVIDOMYCIN AND PROCESS OF PREPARATION

[75] Inventors: Surendra N. Sehgal, Dollard des Ormeaux; Claude Vezina, Oka, both of Canada

[73] Assignee: Ayerst McKenna & Harrison, Inc., Montreal, Canada

[21] Appl. No.: 957,509

[22] Filed: Nov. 3, 1978

[51] Int. Cl.³ ............................................. A61K 35/00
[52] U.S. Cl. ................................... 424/122; 435/169
[58] Field of Search ..................... 424/122; 195/80 R; 435/169

[56] References Cited

PUBLICATIONS

Buchanan et al., Bergey's Manual of Determinative Bacteriology, 8th Ed., The Williams & Wilkins Co., Balto, Md., 1974, pp. 747-748.

*Primary Examiner*—Jerome D. Goldberg
*Attorney, Agent, or Firm*—Arthur E. Wilfond

[57] ABSTRACT

Ravidomycin is produced by culturing *Streptomyces ravidus* NRRL 11,300 in an aqueous nutrient medium. Ravidomycin is useful as an antibacterial agent. Methods for its preparation and use are disclosed.

6 Claims, No Drawings

RAVIDOMYCIN AND PROCESS OF PREPARATION

BACKGROUND OF THE INVENTION

This invention relates to a new composition of matter called ravidomycin, to a process for its preparation and pharmaceutical compositions therefor. Ravidomycin is useful as an antibacterial agent. More specifically, ravidomycin has the property of adversely affecting the growth of gram positive bacteria including *Staphyloccus pyogenes, Streptococcus faecalis* several pathogenic species of the genus Mycobacterium.

SUMMARY OF THE INVENTION

Ravidomycin is a chemical compound producible by culturing a ravidomycin-producing organism in an aqueous nutrient medium. Ravidomycin exhibits antibacterial activity. The ravidomycin-producing organism used for this invention, *Streptomyces ravidus* nov. sp. NRRL 11,300, was obtained from Guatemala soil.

Ravidomycin, characterized by the following data, (a) is bright yellow crystalline compound, m.p. 225° C. with decomposition, after recrystallization from diethyl ether;

(b) is soluble in acetone, methanol, ethanol, chloroform, and sparingly soluble in diethyl ether;

(c) shows a uniform spot on thin layer plates of silica gel;

(d) has a characteristic elemental analysis of about C, 65.73%, H, 6.34%, N, 2.73%;

(e) exhibits the following characteristic absorption maxima in its ultraviolet absorption spectrum (95% v/v ethanol) 286 nm ($E_{1\ cm}^{1\%}$ 696) and 246 nm ($E_{1\ cm}^{1\%}$ 672);

(f) has a characteristic infrared spectrum in chloroform as shown in accompanying FIG. 1, showing bands ($cm^{-1}$) at 3370, 2840, 1725 and 1135.

(g) has a characteristic nuclear magnetic resonance spectrum in deuterochloroform as shown in accompanying FIG. 2.

Ravidomycin is further characterized by:

(h) having minimum inhibitory concentration against various microorganisms as listed in Table 3; and (i) exhibiting a $LD_{50}$ (i.p. mice) of >400 mg/kg.

Ravidomycin is produced by cultivating *Streptomyces ravidus* NRRL 11,300 in an aqueous nutrient medium containing a sources of assimilable carbon and nitrogen and mineral salts under aerobic conditions until substantial antibacterial activity is present in the fermentation mixture by the production of ravidomycin, and isolating ravidomycin from the fermentation mixture. The latter isolation comprises the steps of: filtering the fermentation mixture, extracting the filter cake with methanol or ethanol to produce an extract and separating ravidomycin from the extract.

Ravidomycin is useful for treating bacterial infections in a mammal when administered to said mammal in an antibacterial effective amount.

A convenient form for administering ravidomycin involves a pharmaceutical composition of ravidomycin and a pharmaceutically acceptable carrier.

DETAILED DESCRIPTION

Figure 1:
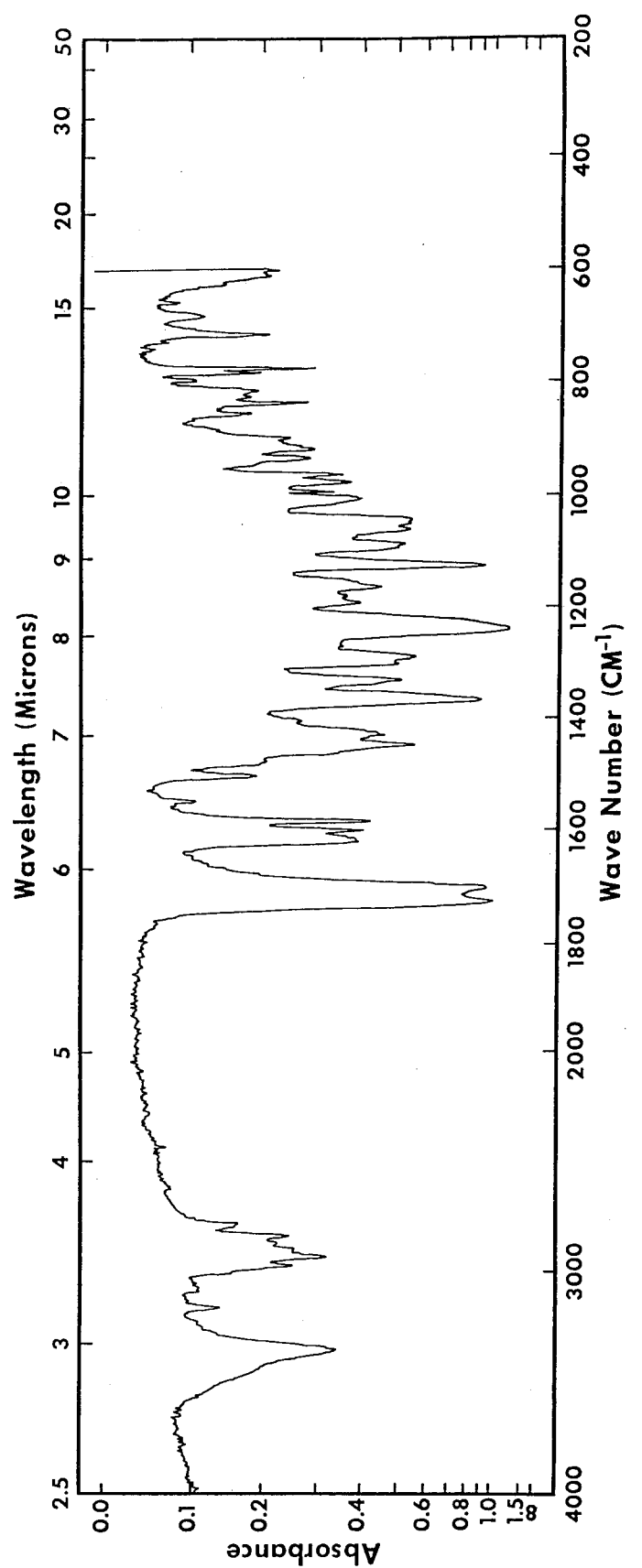

The term "lower alkyl" as used herein means straight chain alkyl radicals containing from one to six carbon atoms and branched chain alkyl radicals containing three or four carbon atoms and includes methyl, ethyl, propyl, butyl, isobutyl, pentyl, hexyl and the like.

The term "lower alkanol" as used herein means straight chain alkanol radicals containing from one to six carbon atoms and a branched chain alkanol radical containing three carbon atoms and includes methanol, ethanol, isopropanol, pentanol, hexanol and the like.

The term "lower alkanoate" as used herein means straight chain alkanoate radicals containing from two to six carbon atoms and a branched chain alkanoate radical containing four carbon atoms and includes acetate, propanoate, 2-methylpropanoate, hexanoate and the like.

The ravidomycin-producing organism used for this invention, *Streptomyces ravidus* nov. sp. NRRL 11,300, was obtained from Guatemala soil and samples thereof have been deposited without restrictions with the Northern Utilization and Research Division, Agricultural Research Service, U.S. Department of Agriculture, Peoria, Ill., U.S.A.

It is to be understood that the invention is not limited to the use of the particular organism herein described, but includes variations and mutants obtained by natural selection or by treatment of the microorganism with, for instance, ultraviolet rays, X-rays, N-methyl-N'-nitro-N-nitrosoguanidine, manganese chloride, camphor, nitrogen mustards, and the like, as well as polyploids of the various mutants.

*Streptomyces ravidus* NRRL 11,300 grows and sporulates well on most media studied. The methods used for its characterization are those of the International Streptomyces Project (ISP) published by E. B. Shirling and D. Gottlieb, Int. J. Syst. Bacteriol., 16, 313–340(1966). The morphology is revealed by phase contrast microscopy (400×) and electron microscopy (10,000×). Aerial mycelium is monopodially branched; sporophores are terminated by long spore chains which form open loops, hooks and sometimes extended spirals of wide diameter. When spore chains are very long, they form very loose spirals without typical arrangements and without a typical number of turns; at 14-day incubation spore chains always consist of more than 10 conidia. Therefore, *S. ravidus* characteristically belongs to group Retinaculum-Apertum as described by T. G. Pridham et. al. Appl. Microbiol., 6, 52–79(1958). Spore color en masse is gray to grayish on all media studied hence the name of the species (*ravidus:* grayish). The substrate mycelium is light brown to yellowish brown to rusty depending on the medium, and the presence of melanin has never been observed. Under the electron microscope, spores are cylindrical to oval in the same chain; they are smooth, 0.9 t 1.5μ.

The cultural characteristics of strain NRRL 11,300 are reported in Table 1. The numbers accompanying colors refer to the Color Harmony Manual Chips used in the guide available from Color Standards Department, Container Corporation of America. Tomato paste-oatmeal agar described by T. G. Pridham et al., Antibiotics Annual, p 947–953 (1956–1957) yields rapid growth and abundant sporulation. (ISP) media also give satisfactory growth and sporulation, but growth is slower on ISP3 than on other media.

TABLE 1

Cultural characteristics of *Streptomyces ravidus* NRRL 11,300

| Culture media[a] | Vegetative mycelium (growth and color[b]) | Aerial mycelium | | |
|---|---|---|---|---|
| | | Development and color[b] | Spores/chain; shape of sporophores | Pigment[b] |
| Tomato paste-oatmeal agar | Rapid and abundant; cream to gray to grayish brown | Abundant grayish | >10 spores/ spiral | Yellowish brown 3 ie |
| Tryptone-yeast extract agar (ISP medium 1, solidified) | Rapid and abundant; yellowish brown | Abundant grayish | >10 spores/ extended spiral | Yellowish brown 3 ie |
| Yeast extract-malt extract agar (ISP medium 2) | Rapid and abundant; yellowish brown 3 ic | Abundant cream 3 ba | >10 spores/ extended spiral | Yellowish brown 3 ie |
| Oatmeal agar (ISP medium 3) | Slow but eventually abundant; yellowish brown | Slow but eventually abundant; gray 3 fe | >10 spores/ extended spiral | Light Brown 3 ie |
| Inorganic salts-starch agar (ISP medium 4) | Rapid and very abundant; light brown | Rapid and very abundant; gray 2 ih | | None |
| Glycerol-asparagine agar (ISP medium 5) | Relatively slow but eventually very abundant; rust 4 ng | Very abundant; gray 2 fe | >10 spores/ extended spiral | Brown 4 lg |

[a] For composition of ISP media refer to E. B. Shirling and D. Gottlieb, Int. J. Syst. Bacteriol., 16, 313-340(1966); in this study Bacto dehydrated media (Difco Laboratories, Detroit, Mich.) were used.
[b] Number and letters following color refer to Color Harmony Manual Chips, Color Standards Department, Container Corporation of America, 38 South Dearborn Street, Chicago, Ill. 60603, U.S.A.

The physiological characteristics of *Streptomyces ravidus* NRRL 11,300 are summarized in Table 2. Good growth and sporulation are observed in the temperature range of 20° to 32° C., but no growth takes place at 37° C. (even after 14 days of incubation). Good growth and sporulation are also observed in the pH range of 6 to 8. No melanoid pigment is produced and no $H_2S$ can be detected. Nitrate is reduced after 14 days, but not after 7 days of incubation. The organism is resistant to 10 μg streptomycin per ml.

TABLE 2

Physiological characteristics of *Streptomyces ravidus* NRRL 11,300

| Parameters | Reactions and other observations |
|---|---|
| Hydrolysis of starch (ISP medium 4) | Weak |
| Decomposition of cellulose | Negative |
| Production of hydrogen sulfide ($H_2S$) (ISP medium 6) | Negative |
| Production of tyrosinase (ISP medium 7) | Negative (melanin-negative) |
| Nitrate reduction (ISP medium 8) | Positive at 14 days, Negative at 7 days |
| Carbohydrate utilization (ISP medium 9)[a] | Good growth on D-glucose, D-xylose, i-inositol Slight growth (14 days) on: D-fructose No growth on: L-arabinose, rhamnose, raffinose, D-galactose, sucrose, D-mannitol, cellulose, salicin |
| Streptomycin (10 μg/ml) | Resistant |
| Reaction to pH | Growth at pH 5-8 |
| Reaction to temperature | Growth at 20°-35° C.; no growth at 37° C. |

[a] Bacto-Carbon Utilization agar was used as the basal medium; light growth without carbohydrate added.

*Streptomyces ravidus* NRRL 11,300 does not utilize a wide variety of carbohydrates. It differs in its carbohydrate utilization and other characteristics from all species of streptomycetes of the gray series (see for example Table 17.42f, Bergey's Manual of Determinative Bacteriology, Eighth Ed., R. E. Buchanan and N. E. Gibbons, Ed., The Williams & Wilkins Company, Baltimore, 1974. Cellulose is not utilized, and starch is only weakly hydrolyzed, if at all. Some growth is observed on Carbohydrate Utilization Medium (ISP9) with no added carbohydrate even when the spore inoculum has been washed twice in distilled water, indicating that this streptomycete possibly fixes atmospheric carbon dioxide. Results in Table 2 take this observation into account. D-glucose, D-xylose and i-inositol support rapid and abundant growth, whereas D-fructose supports slight growth at 14 days. All other sugars tested and salicin are not utilized.

The environment and nutritional requirements for the fermentation of *Streptomyces ravidus* NRRL 11,300 are similar to those necessary for the production of antibiotics by other aerobic microorganisms. Thus, aerobiosis can be sustained in a liquid nutrient medium inoculated with a sterile culture incubated in flasks placed on shaking machines. For industrial production, metal tanks with internal aeration and agitation by means of paddles can be substituted. Ravidomycin is also produced by surface cultivation. The microorganism requires as nutrient elements assimilable carbon and organic nitrogenous substances. The presence of mineral salts is desirable. Cultivation is best effected when the initial pH of the culture medium is between 6.5 and 7.5, the optimum pH being around 6.8-7.3.

The utilizable sources of assimilable carbon for the production of the antibiotic are very diverse, there being included sugars such as D-glucose, D-xylose and D-fructose, dextrin, starches of different types of origin, glycerol and (other polyalcohols), inositol and animal and vegetable fats, as well as esters thereof. The sources of organic assimilable nitrogen which activity stimulate growth and favor production of ravidomycin are substances such as soybean meal, cotton meal and other vegetable meals (whole or partially or totally defatted), meat flours or animal viscera, various peptones, casein hydrolystates, soybean hydrolysates, yeast hydrolysates, lactalbumin, wheat glutins, distillers solubles, corn steeps, molasses, urea and amino acids.

Mineral salts, such as the chlorides, nitrates, sulfates, carbonates and phosphates of sodium, potassium, ammonium and calcium, should be included in appropriate concentrations. The nutritive medium should contain a number of trace elements such as magnesium, iron, manganese, and zinc.

The inoculum of the above medium for the fermentation is provided with a fresh slant of *Streptomyces ravidus*.

Under the described conditions and with the temperature of cultivation at about 20°–35° C., preferably at about 25° C., maximum production of ravidomycin is obtained in from about two to about eight days in tanks.

Thereafter, a variety of procedures may be employed in the isolation and purification of ravidomycin, for example, solvent extraction, partition chromatography, silica gel chromatography, liquid-liquid distribution in a Craig apparatus, and crystallization from solvents. Solvent extraction procedures are preferred for commercial recovery inasmuch as they are less time consuming and less expensive.

Ravidomycin may be harvested by one of the following methods.

(a) The fermentation mixture is extracted with a substantially water-immiscible solvent, preferably a lower alkanol for example n-butanol, n-pentanol or the commercial mixture of pentaols known as "Pentasol" or n-hexanol, or a substantially water-immiscible lower alkyl lower alkanoate, for example, ethyl acetate, butyl acetate, amyl acetate or the commercially available mixture of amyl acetates, or a substantially water-immiscible halogenated aliphatic hydrocarbon having one to three carbon atoms, for example, chloroform, methylene dichloride or dichloroethane. The extracts are dried and concentrated under reduced pressure to yield an oily residue which is in turn extracted with a water-miscible solvent, preferably a lower alkanol, for example methanol or ethanol. Said last-named extracts are filtered through diatomaceous earth ("Celite"), and the filtrate is concentrated under reduced pressure to yield an oily residue containing crude ravidomycin.

(b) The fermentation mixture is filtered through a pad of diatomaceous earth ("Celite") and the filter cake containing the mycelium is extracted as described below under (c). The filtrate, i.e. the mycelium-free fermentation mixture, is extracted several times with a substantially water-immiscible solvent, for example, a lower alkanol, lower alkyl lower alkanoate or halogenated aliphatic hydrocarbon as exemplified above in section (a). The extracts are dried and concentrated under reduced pressure to yield an oily residue which is extracted with a water-miscible solvent, preferably a lower alkanol, for example methanol or ethanol. Said last-named extracts are treated in the same manner as described above under (a) to yield an oily residue containing crude ravidomycin.

(c) The mycelium is separated from the fermentation mixture and extracted with a suitable water-miscible solvent, preferably a lower alkanol, for example methanol or ethanol. The extract is concentrated by evaporation to the aqueous phase, which in turn is extracted with a substantially water-immiscible solvent, such as a lower alkyl lower alkanoate, halogenated aliphatic hydrocarbon or a substantially water-immiscible lower alkanol as described above or an aromatic hydrocarbon, for example benzene or toluene. The latter extract is evaporated under reduced pressure to yield an oily residue containing crude ravidomycin.

The crude ravidomycin obtained by any of the processes described in sections (a), (b) or (c) is then be purified by a variety of methods, for example, see above. Preferred methods include absorption of the crude ravidomycin on an absorbent, for instance charcoal or silica gel, from a solution in a substantially nonpolar, first solvent, followed by elution therefrom with a second solvent, more polar than said first solvent.

The antibacterial activity of ravidomycin is demonstrable in standard tests used for this purpose for example, in the tests described in "Antiseptic, Disinfectants, Fungicides and Sterilization" G. F. Reddish Ed. 2nd edition, Lea and Febiger, Philadelphia, 1957 or by D. C. Cerone and W. A. Randall in "Assay Methods of Antibiotics", Med. Encycl. Inc., New York, 1955.

By using the test for antibacterial activity, ravidomycin is an antibacteria agent having the property of adversely affecting the growth of gram positive bacteria including *Staphylococcus pyogenes, Streptococcus faecalis* and several pathogenic species of the genus Mycobacterium. The minimum inhibitory concentration of ravidomycin against various bacteria using the standard tube dilution procedure is shown in Table 3.

TABLE 3

Minimum inhibitory concentration (MIC) of ravidomycin

| BACTERIA | MIC ($\mu$/ml) |
|---|---|
| *Staphylococcus pyogenes* Pc$^S$ | 3.2 to 12.5 |
| *Staphylococcus pyogenes* Pc$^R$ | 3.2 |
| *Streptococcus faecalis* | <0.2 to 0.4 |
| *Escherichia coli* | 100 |
| *Enterobacter aerogenes* | 50 |
| *Salmonella pullorum* | 100 |
| *Pseudomonas aeruginosa* | >100 |
| *Proteus mirabilis* | >100 |
| *Proteus vulgaris* | >100 |
| *Klebsiella pneumoniae* | 25 |
| *Serratia marcescens* | 50 |
| *Mycobacterium tuberculosis* var. *hominis* | 1 to 5 |
| Photochromogenic mycobacteria (Group I)[a] | 25 |
| Scotochromogenic mycobacteria (Group II)[a] | 5 |
| *Mycobacterium fortuitum* (Group IV)[a] | 0.5 |

[a]According to the classification of Runyon cited by Valerie Beer and V. Bonifas, Les mycobacteries, Schweiz. med. Wschr., 105(31), 984–987 (1975).
The acute intraperitoneal LD$_{50}$ in mice is greater than 400 mg/kg of body weight.

When ravidomycin of this invention is employed as an antibacterial agent in warm-blooded animals, e.g. rats, it may be used alone or in combination with pharmaceutically acceptable carriers, the proportion of which is determined by the solubility and chemical nature of the compound, chosen route of administration and standard biological practice. For example, an antibacterial effective amount of ravidomycin can be administered orally in solid form containing such excipients as starch, sugar, certain types of clay and so forth. Similarly, such an amount can also be administered orally in the form of solutions or suspensions, or injected parenterally. For parenteral administration ravidomycin can be used in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The dosage of ravidomycin will vary with the form of administration and the particular compound chosen.

Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compound of this invention is most desirably administered at a concentration level that will generally afford antibacterial effective results without causing any harmful or deleterious side effects.

When used as an antibacterial agent, ravidomycin is administered at a dose about 5 to 250 mg per kilogram of body weight per day, although the aforementioned variations will occur. However, a dosage level that is in the range of from about 10 mg to about 100 mg per kilogram of body weight per day is most desirably employed in order to achieve effective results.

In addition, the antibacterial agent can be employed topically. For topical application it may be formulated in the form of solutions, creams, or lotions in pharmaceutically acceptable vehicles containing 0.1-5 percent, preferably 2 percent of the agent, and may be administered topically to the infected area of the skin.

Ravidomycin, as an antibacterial agent, can also be used for cleaning and disinfecting laboratory equipment, surgical instruments, locker rooms, or shower rooms of sensitive bacteria organisms. For such purposes it is preferred to use 0.1-10% solutions of ravidomycin in a lower alkanol, preferably methanol, diluted with 10-100 volumes of water containing 0.001-0.1% of a non-ionic surface-active agent, for example, polysorbate 80 U.S.P., immediately before applying it to the objects to be cleaned and disinfected.

PREPARATION

In a preferred embodiment of this invention ravidomycin is prepared in the following manner.

A suitable fermenter is charged with production medium given in Example 1. After sterilization and cooling, the medium is inoculated with a first stage inoculum preparation of *Streptomyces ravidus*.

A maximum titre of 400-500 μg/ml of the antibiotic is reached in the fermentation mixture after 2-8 days, usually after about 5 days, as determined by fluorometry or by the cup plate method and *Staphylococcus aureus* as the test organism. The mycelium is harvested by filtration with diatomaceous earth. Ravidomycin is then extracted from the mycelium with a water-miscible solvent, for example a lower alkanol, preferably methanol or ethanol. The latter extract is then concentrated, preferably under reduced pressure, and the resulting aqueous phase is extracted with a water-immiscible solvent. A preferred water-immiscible solvent for this purpose is methylene dichloride although chloroform, carbon tetrachloride, benzene, n-butanol, ethyl acetate the like may also be used. The latter extract is concentrated, preferably under reduced pressure, to afford the crude product as an oil.

The product can be purified further by a variety of methods. Among the preferred methods of purification to dissolve the crude product in a substantially non-polar, first solvent, for example petroleum ether, benzene or hexane, and to treat the resulting solution with a suitable absorbent, for example charcoal or silica gel, so that the antibiotic becomes absorbed on the absorbant. The absorbant is then separated and washed or eluted with a second solvent more polar than the first solvent, for example ethyl acetate, methylene dichloride, acetone or mixtures thereof. A mixture of methylene dichloride and diethyl ether or a mixture of hexane and acetone is preferred. Thereafter, concentration of the wash solution or eluate affords substantially pure ravidomycin. Further purification is obtained by partial precipitation with a non-polar solvent, for example, petroleum ether, hexane, pentane and the like, from a solution of the ravidomycin in a more polar solvent, for example, diethyl ether, ethyl acetate, benzene and the like. Still further purification is obtained by column chromatography, preferably employig silica gel and 20 to 40% acetone in hexane, and by crystallization of the ravidomycin, preferably from diethyl ether or acetone.

CHARACTERIZATION (a) Purified ravidomycin is bright yellow crystalline compound, m.p. 255° C. with decomposition, after recrystallization from diethyl ether;

(b) Ravidomycin is soluble in acetone, methanol, ethanol, chloroform, and sparingly soluble in diethyl ether;

(c) Ravidomycin shows a uniform spot on thin layer plates of silica gel G (E. Merck, A. G. Darmstadt) developed with a variety of thin layer chromatography solvent systems, for example, acetone-hexane 60:40 ($R_f$=0.56); ethanol-benzene 20:80 ($R_f$=0.62) and methanol-chloroform 20:80 ($R_f$=0.77);

(d) Ravidomycin obtained from two successive fermentation batches gave the following values on repeated elemental analysis:

|  |  |  | Average |
| --- | --- | --- | --- |
| C % | 65.91 | 65.55 | 65.73 |
| H % | 6.46 | 6.22 | 6.34 |
| N % | 2.67 | 2.8 | 2.73; |

Figure 2:
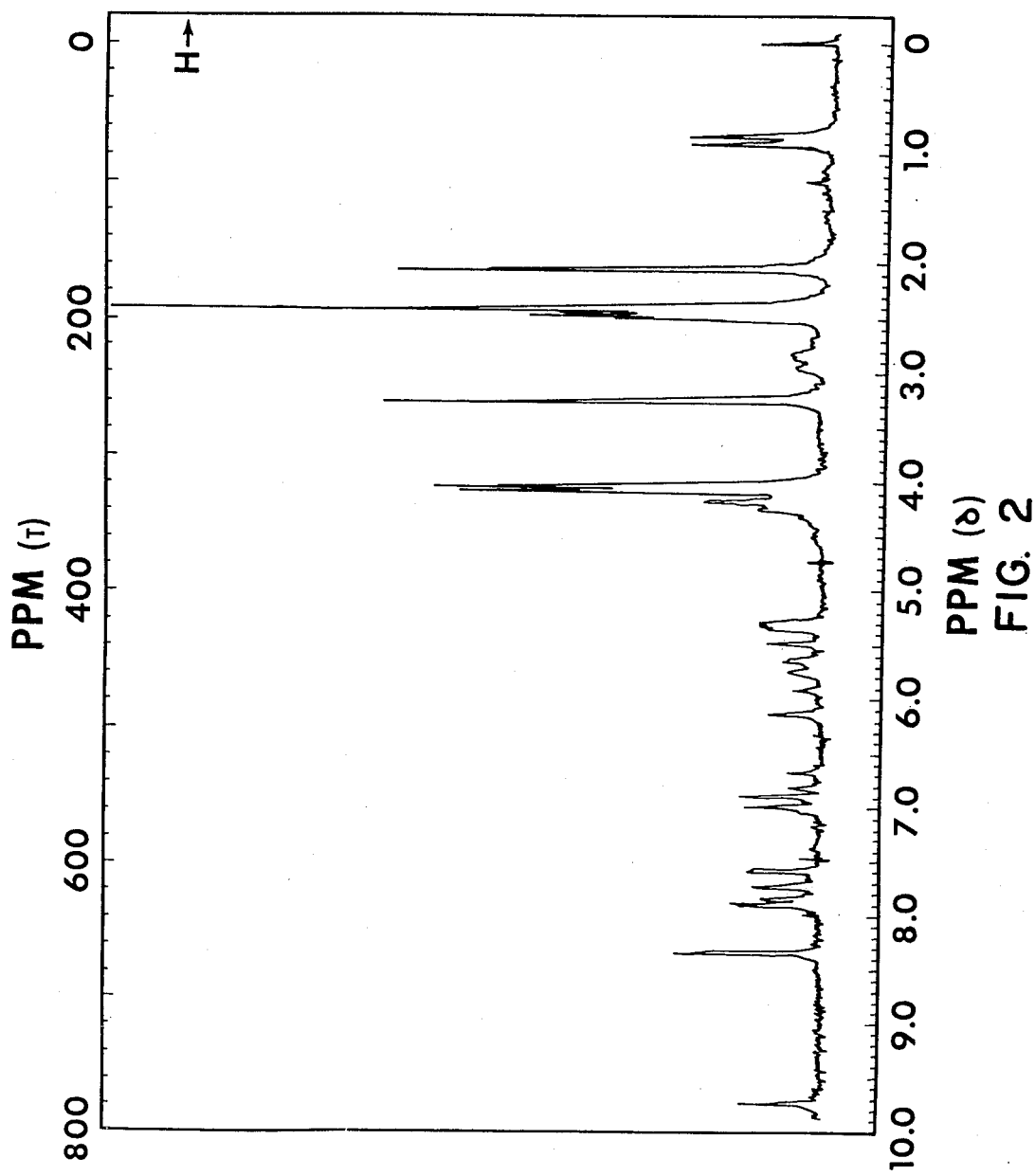

(e) Ravidomycin exhibits the following characteristic absorption maxima in its ultraviolet absorption spectrum (95% v/v ethanol) 286 nm ($E_1\ _{cm}^{1\%}$ 696) and 246 nm ($E_1\ _{cm}^{1\%}$ 672);

(f) The infrared absorption spectrum of ravidomycin in chloroform is reproduced in FIG. 1 and shows characteristic absorption bands at 3370 cm$^{-1}$, 2840 cm$^{-1}$, 1725 cm$^{-1}$ and 1135 cm$^{-1}$;

(g) The nuclear magnetic resonnance spectrum of rapamycin in deuterochloroform is reproduced in FIG. 2;

(h) The minimum inhibitory concentration of ravidomycin against various microorganisms is listed in Table 3;

(i) Ravidomycin exhibits a $LD_{50}$ (i.p. mice) of 400 mg/kg; and (j) Ravidomycin causes 50% reduction in colon 38 tumor weight at dose level of 25 mg/kg. evaluated on 20th day of implantation in mice.

The following example illustrates further this invention.

EXAMPLE 1

Microorganism

*Streptomyces ravidus* NRRL 11,300 was grown and maintained on oatmeal-tomato paste agar slants (T. G. Pridham, et al., Antibiotic Annual 1956-1957, Medical Encyclopedia Inc., New York, p. 947) and in Roux bottles containing the same medium. Good growth was obtained after 7 days of incubation at 28° C. Spores from one Roux bottle were washed off and suspended into 50 ml of sterile distilled water. This suspension was used to inoculate the first state inoculum.

The first-stage inoculum medium consisted of Emerson broth [R. L. Emerson et al., J. Bacteriol., 52,357 (1946)] beef extract 0.4%; peptone, 0.4%; sodium chloride, 0.25%; yeast extract, 0.1%; and glucose, 1% pH 7.0; flasks containing the above medium were inoclated with 1% of the spore suspension described above. The inoculated flasks were incubated for 30 hrs. at 25° C. on a reciprocating shaker set at 65 r.p.m. (4" stroke).

Production stage

The production stage was run in 250-liter New Brunswick fermenters Model F-250, equipped with automatic antifoam addition system and pH recorder-controller. The fermenters were charged with 160 liters of an aqueous production medium consisting of the following constituents:

| | |
|---|---|
| Glycerol | 1.0% |
| Tomato paste | 1.0% |
| Corn meal | 0.5% |
| glucose (Cerelose) | 1.0% |
| $MgSO_4$ | 0.025% |
| "Blackstrap" molasses | 2.0% |
| hydrolyzed casein (NZ-Case) Sheffield Chemical, Norwich, New York) | 0.5% |
| Mazur DF-143PX (Mazur Chemical Corp., Gurnee, Illinois) | 0.1% |
| pH 7.0 to 7.2 after sterilization | |

The fermenters were sterilized at 121° C. for 45 minutes, cooled and inoculated with one flask (2% inoculum) of first stage inoculum. Incubation temperature: 28° C.; aeration: 0.5 vol/vol/min.; agitation: 250 r.p.m.

A titre of ca. 500 μg/ml, determined by spectrophotofluorometric assay, was reached in 5 days. The fermentation was stopped.

Extraction and isolation of ravidomycin was performed by one of the following methods.

Extraction (a) The fermentation mixture was extracted twice with 1 v/v of n-butanol. The combined butanol extracts were washed with 1 v/v of water, dried with anhydrous sodium sulfate and evaporated to dryness under reduced pressure to yield a residue. The oily residue was extracted three times with 2 liters of methanol. The combined methanol extracts were passed through diatomaceous earth ("Celite") and evaporated to dryness to yield an oily residue containing crude ravidomycin.

(b) The fermentation mixture was filtered over diatomaceous earth ("Celite"). The filtrate was extracted twice with 1 v/v of ethyl acetate. The ethyl acetate extracts were washed with 1 volume of water, dried with anhydrous sodium sulfate and evaporated under reduced pressure to dryness. The residue was extracted twice with 1 liter of methanol. The methanol extracts were evaporated under reduced pressure to yield an oily residue containing crude ravidomycin.

(c) The mycelium obtained as described under section (b) was washed with 1 to 2 volumes of water. The washed mycelium was extracted three times with 5 volumes of methanol per weight of wet mycelium each time. The methanolic extracts were pooled and concentrated under reduced pressure to a small volume of an aqueous phase containing approximately 10% v/v of methanol. This aqueous phase was extracted three times with 1 vol. of methylene chloride; the methylene chloride extracts were combined, dried with anhydrous sodium sulfate and evaporated to yield an oily residue.

The oily residue obtained from either one of the above methods was dissolved in benzene and charged on a short silica gel G column which was then washed with benzene, hexane and 20% acetone in hexane respectively. The active product was eluted with 30% acetone in hexane. On evaporation, the eluant yielded a yellow precipitate of crude active product. The precipitate was dissolved in 40% acetone in hexane and subjected to column chromatography on silica gel G column in the same solvent mixture. The fractions containing active product were combined and evaporated to dryness under vacuum. The pure product was crystallized from diethyl ether. Recovery yields were about 200 μg/ml of ravidomycin.

We claim:

1. Ravidomycin which:
   (a) is bright yellow crystalline compound, m.p. 255° C. with decomposition, after recrystallization from diethyl ether;
   (b) is soluble in acetone, methanol, ethanol, chloroform, and sparingly soluble in diethyl ether;
   (c) shows a uniform spot on thin layer plates of silica gel;
   (d) has a characteristic elemental analysis of about C, 65.73%, H, 6.34%, N, 2.73%;
   (e) exhibits the following characteristic absorption maxima in its ultraviolet absorption spectrum (95% v/v ethanol) 286 nm ($E_{1\ cm}^{1\%}$ 696) and 246 nm ($E_{1\ cm}^{1\%}$ 672);
   (f) has a characteristic infrared spectrum in chloroform as shown in accompanying FIG. 1; and
   (g) has a characteristic nuclear magnetic resonance spectrum in deuterochloroform as shown in accompanying FIG. 2.

2. A process for the production of ravidomycin which comprises cultivating Streptomyces ravidus NRRL 11,300 in an aqueous nutrient medium containing a source of assimilable carbon and nitrogen and mineral salts under aerobic conditions until substantial antibacterial activity is present in the fermentation mixture by the production of ravidomycin, and isolating ravidomycin from said fermentation mixture.

3. The process as claimed in claim 2 in which the cultivation is carried out at a temperature ranging from 20° to 35° C. and at an initial pH of between 6.5 and 7.5.

4. The process according to claim 2 in which the isolation comprises filtering the fermentation mixture, extracting the filter cake with methanol or ethanol to produce an extract and separating the ravidomycin from the extract.

5. A method of treating bacterial infections in a mammal, which comprises administering to said mammal an antibacterial effective amount of ravidomycin, as claimed in claim 1.

6. A pharmaceutical composition comprising an antibacterial effective amount of ravidomycin, as claimed in claim 1, and a pharmaceutically acceptable carrier.

* * * * *